United States Patent

Buchmann et al.

Patent Number: 5,559,134
Date of Patent: Sep. 24, 1996

[54] LEUKOTRIENE-$B_4$ ANTAGONISTS, PROCESS FOR THEIR PRODUCTION AND THEIR USE AS PHARMACEUTICAL AGENTS

[75] Inventors: Bernd Buchmann; Werner Skuballa; Josef Heindl; Wolfgang Fröhlich; Roland Ekerdt; Claudia Giesen, all of Berlin, Germany

[73] Assignee: Schering Aktiengesellschaft, Berlin, Germany

[21] Appl. No.: 387,863

[22] PCT Filed: Aug. 19, 1993

[86] PCT No.: PCT/EP93/02225

§ 371 Date: Mar. 23, 1995

§ 102(e) Date: Mar. 23, 1995

[87] PCT Pub. No.: WO94/04522

PCT Pub. Date: Mar. 3, 1994

[30] Foreign Application Priority Data

Aug. 25, 1992 [DE] Germany .......... 42 28 201.2

[51] Int. Cl.$^6$ .......... C07D 213/79; C07C 69/712; A61K 31/215
[52] U.S. Cl. .......... 514/336; 546/14; 546/316; 546/318; 546/323; 546/326; 546/283.7; 546/283.1; 549/452; 549/454; 560/56; 562/473; 564/171; 514/354; 514/355; 514/356; 514/463; 514/532; 514/568; 514/617
[58] Field of Search .......... 546/316, 318, 546/323, 326, 283; 560/56; 562/473; 564/171; 514/354, 355, 356, 568, 532, 617, 336, 463; 549/452, 454

[56] References Cited

FOREIGN PATENT DOCUMENTS

| | | |
|---|---|---|
| 0104885 | 4/1984 | European Pat. Off. .......... 514/354 |
| 0306959 | 3/1989 | European Pat. Off. .......... 514/354 |
| 0375457 | 6/1990 | European Pat. Off. .......... 514/354 |

*Primary Examiner*—Zinna Northington Davis
*Attorney, Agent, or Firm*—Millen, White, Zelano, & Branigan, P.C.

[57] ABSTRACT

The invention relates to leukotriene-$B_4$ antagonists of formula I

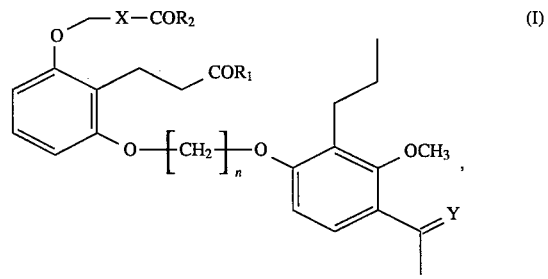

in which n represents a whole number from 2 to 5, X represents a direct bond, 1 to 6 methylene units, an ortho-, meta- or para-substituted phenyl ring or a meta- or para-substituted pyridine ring, Y represents a bond to a hydrogen atom and simultaneously to a hydroxy group, a double-bound oxygen atom or —O—$CH_2$—$CH_2$—O—, $R_1$ and $R_2$ represent the radical OH, —O—($C_1$-$C_4$)—alkyl, O—($C_3$-$C_6$)—cycloalkyl, —O—($C_6$-$C_{10}$)—aryl, —O—($C_7$-$C_{12}$)—aralkyl, O—($CH_2$)—CO— ($C_6$-$C_{10}$)—aryl or the radical $NHR_3$ with $R_3$ meaning hydrogen, ($C_1$-$C_4$)—alkyl, ($C_3$-$C_6$)—cycloalkyl or ($C_7$-$C_{12}$)—aralkyl as well as their salts with physiologically compatible bases and their cyclodextrin clathrates.

11 Claims, No Drawings

LEUKOTRIENE-$B_4$ ANTAGONISTS, PROCESS FOR THEIR PRODUCTION AND THEIR USE AS PHARMACEUTICAL AGENTS

This application was filed under 35 U.S.C. §371 from PCT/EP93/02225 filed Aug. 19, 1993.

The invention relates to new leukotriene-$B_4$ antagonists, process for their production and their use as pharmaceutical agents.

Leukotriene $B_4$ ($LTB_4$) was discovered in 1979 by B. Samuelsson et al. as a metabolite of the arachidonic acid. In the biosynthesis, leukotriene $A_4$ is formed by the enzyme 5-lipoxygenase first as central intermediate product, which then is converted by a specific hydrolase to the $LTB_4$.

KEY:
Arachidonsäure=arachidonic acid
Leukotrien $A_4$ ($LTA_4$)=leukotriene $A_4$ ($LTA_4$)
Glutathion - S-transferase=glutathione - S-transferase
Leukotrien $B_4$ ($LTB_4$)=leukotriene $B_4$ ($LTB_4$)
Leukotrien $C_4$ ($LTC_4$)=leukotriene $C_4$ ($LTC_4$)

It is known concerning $LTB_4$ that it causes the adhesion of leukocytes on the blood vessel wall. $LTB_4$ is chemotactically effective, i.e., it triggers a directed migration of leukocytes in the direction of a gradient of increasing concentration. Furthermore, it indirectly changes the vascular permeability based on its chemotactic activity, and a synergism with prostaglandin $E_2$ is observed. $LTB_4$ obviously plays a decisive role in inflammatory, allergic and immunological processes.

Leukotrienes and especially $LTB_4$ are involved in skin diseases, which are accompanied by inflammatory processes (increased vascular permeability and formation of edemas, cell infiltration), increased proliferation of skin cells and itching, such as, for example, in eczemas, erythemas, psoriasis, pruritus and acne. Pathologically increased leukotriene concentrations are involved either causally in the development of many dermatitides or there is a connection between the persistence of the dermatitides and the leukotrienes. Clearly increased leukotriene concentrations were measured, for example, in the skin of patients with psoriasis or atopic dermatitis.

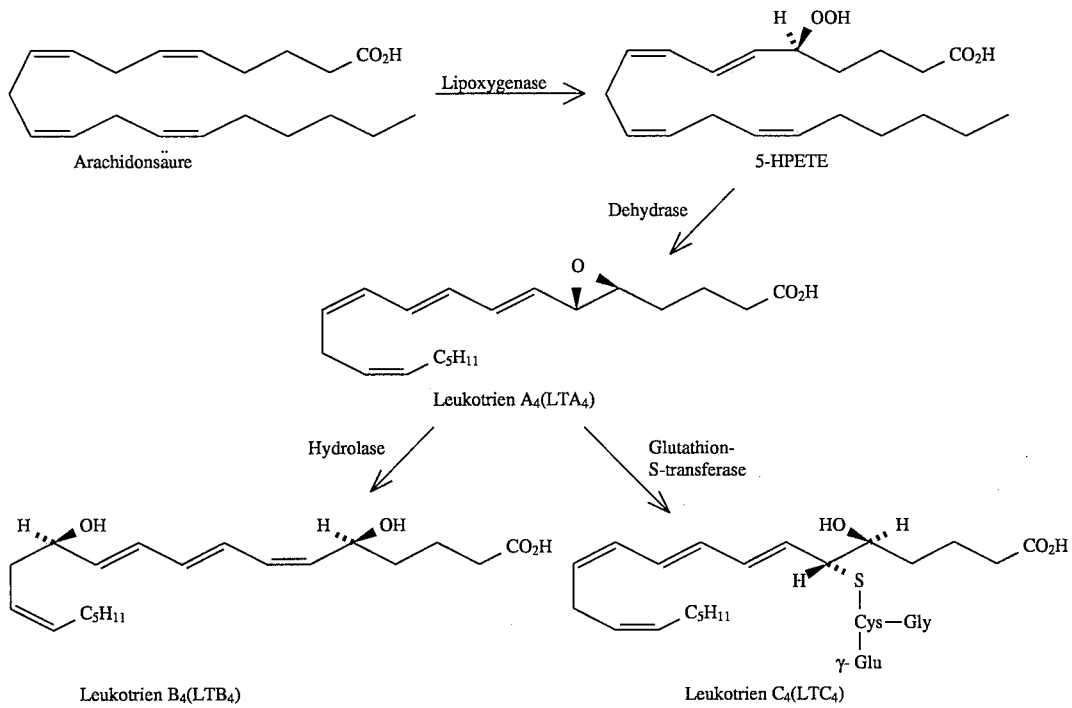

The nomenclature of the leukotrienes can be gathered from the following works:
a) B. Samuelsson et al., Prostaglandins 19, 645 (1980); 17, 785 (1979).
b) C. N. Serhan et al., Prostaglandins 34, 201 (1987).

The physiological and especially the pathophysiological importance of leukotriene $B_4$ is summarized in several more recent works: a) The Leukotrienes, Chemistry and Biology eds. L. W. Chakrin, D. M. Bailey, Academic Press 1984. b) J. W. Gillard et al., Drugs of the Future 12, 453 (1987). c) B. Samuelsson et al., Science 237, 1171 (1987). d) C. W. Parker, Drug Development Research 10, 277 (1987). It follows from the above that $LTB_4$ is an important inflammation mediator for inflammatory diseases, in which leukocytes invade the affected tissue. The effects of $LTB_4$ are triggered on the cellular plane by the bond of $LTB_4$ on a specific receptor.

Leukotrienes and especially $LTB_4$ are also involved in the diseases of internal organs, for which an acute or chronic inflammatory component was described, e.g.: joint diseases (arthritis); diseases of the respiratory tract (asthma, rhinitis and allergies); inflammatory intestinal diseases (colitis); as well as reperfusion damages (to the heart, intestinal or renal tissues), which result from the temporary pathological obstruction of blood vessels.

Further, leukotrienes and especially $LTB_4$ are involved in the disease of multiple sclerosis and in the clinical picture of shock (triggered by infections, burns or in complications in kidney dialysis or. other separately discussed perfusion techniques).

Leukotrienes and especially $LTB_4$ further have an effect on the formation of white blood cells in the bone marrow, on the growth of unstriped muscle cells, of keratinocytes and of B-lymphocytes. $LTB_4$ is therefore involved in diseases with inflammatory processes and in diseases with pathologically increased formation and growth of cells.

For example, leukemia or arteriosclerosis represent diseases with this clinical picture.

By the antagonizing of the effects, especially by $LTB_4$, the active ingredients and their forms of administration of this invention are specific medicines for diseases of humans and animals, in which especially leukotrienes play a pathological role.

Besides the therapeutic possibilities, which can be derived from an antagonizing of $LTB_4$ action with $LTB_4$ analogs, the usefulness and potential use of leukotriene-$B_4$ agonists for the treatment of fungus diseases of the skin were also able to be shown (H. Katayama, Prostaglandins 34, 797 (1988)).

From EP 405116, compounds with a phenylpropionic acid structure, which have leukotriene-$B_4$-antagonistic properties, are already known.

Compounds have been found that surprisingly strongly antagonize the effect of the natural $LTB_4$.

The invention relates to leukotriene-$B_4$ antagonists of formula I

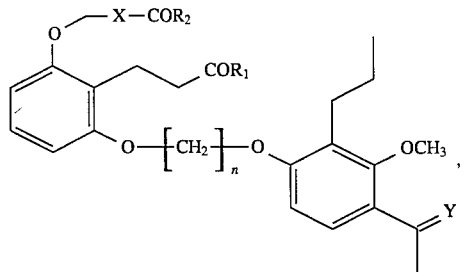

(I)

in which n represents a whole number from 2 to 5,

X represents a direct bond, 1 to 6 methylene units, an ortho-, meta- or para-substituted phenyl ring or a meta- or para-substituted pyridine ring, Y represents a bond to a hydrogen atom and simultaneously to a hydroxy group, a double-bound oxygen atom or $-O-CH_2-CH_2O-$, $R_1$ and $R_2$ represent the radical OH, $-O-(C_1-C_4)-$alkyl, $O-(C_3-C_6)-$cycloalkyl, $-O-(C_6-C_{10})-$aryl, $-O-(C_7-C_{12})-$aralkyl, $O-(CH_2)-CO-C_6-C_{10})-$aryl aryl or the radical $NHR_3$ with $R_3$ meaning hydrogen, $(C_1-C_4)-$alkyl, $(C_3-C_6)-$cycloalkyl or $(C_7-C_{12})-$aralkyl as well as their salts with physiologically compatible bases and their cyclodextrin clathrates.

$R_1$ and $R_2$ as $C_1-C_4$ alkoxy group can mean: methoxy, ethoxy, n-propoxy, isopropoxy, n-butoxy, sec-butoxy and tert-butoxy.

As radicals $(C_3-C_6)$—cycloalkyl in the definition of $R_1$ and $R_2$, cyclopropyl, cyclobutyl, cyclopentyl, cyclohexyl are to be considered.

As radicals $(C_6-C_{10})$—aryl in the definition of $R_1$ and $R_2$, phenyl, 1-naphthyl, 2-naphthyl are to be considered.

As radicals $O-(CH_2)-CO-(C_6-C_{10})$—aryl in the definition of $R_1$ and $R_2$, for example, phenacyl is to be considered.

The following groups finally represent the radicals $(C_7-C_{12})$—aralkyl in the definitions of $R_1$ and $R_2$: benzyl, phenethyl, 3-phenylpropyl, 4-phenylbutyl, 1-methyl-3-phenylpropyl, 1-methyl-2-phenyl-ethyl, etc.

Inorganic and organic bases are suitable for salt formation, as they are known to one skilled in the art for forming physiologically compatible salts. For example, there can be mentioned alkali hydroxides, such as sodium hydroxide and potassium hydroxide, alkaline-earth hydroxides, such as calcium hydroxide, ammonia, amines, such as ethanolamine, diethanolamine, triethanolamine, N-methylglucamine, morpholine, tris-(hydroxymethyl)-methylamine, etc.

To attain the cyclodextrin clathrates, the compounds of formula I are reacted with α-, β- or γ-cyclodextrin. Preferred are the β-cyclodextrin clathrates. In addition, the invention relates to a process for the production of leukotriene-$B_4$ antagonists of formula I, characterized in that in a way known in the art, a compound of formula II

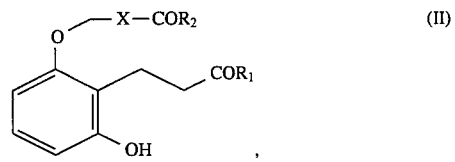

(II)

in which X, $R_1$, and $R_2$ have the above-indicated meaning, is reacted in the presence of cesium, lithium or potassium carbonate with a compound of formula III

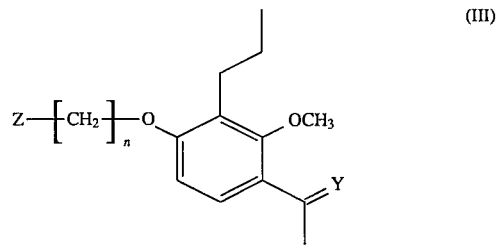

(III)

in which n and Y has the above-indicated meaning, and Z can be either a halogen atom or a sulfonate, such as, for example, tosylate, mesylate or trifluorosulfonate, and optionally the protective groups are cleaved, the methyl ketone is reduced, the ester groups are saponified, carboxyl groups are esterified or the obtained acids of formula I are reacted with organic or inorganic bases or cyclodextrins.

The above-mentioned process (II+III=>I) is performed in organic solvents, such as, e.g., dimethylformamide, at temperatures between 0° C. and 100° C., preferably at temperatures between 20° C. and 60° C. with stirring in the course of 5–24 hours in the presence of cesium, lithium or potassium carbonate.

The reduction of the carbonyl group (Y=0) takes place preferably with sodium borohydride under the usual conditions. The hydroxy compounds obtained can optionally be separated into the optical antipodes.

The saponification of the esters of formula I is performed according to the methods known to one skilled in the art, such as, for example, with basic catalysts.

The introduction of ester group $-COR_1$, in which $R_1$ represents an O-alkyl group with 1–4 C atoms, takes place according to the methods known to one skilled in the art. The carboxy compounds are reacted, for example, with diazohydrocarbons in a way known in the art. The esterifications with diazohydrocarbons takes place, e.g., in that a solution of the diazohydrocarbon in an inert solvent, preferably in diethyl ether, is mixed with the carboxy compound in the same or in another solvent, such as, e.g., methylene chloride. After completion of the reaction in 1 to 30 minutes, the solvent is removed and the ester is purified in the usual way. Diazoalkanes are either known or can be produced according to known methods [Org. Reactions Vol. 8, pages 389–394 (1954)].

The introduction of ester group $-COR_1$, in which $R_1$ represents an O-aryl group, takes place according to the methods known to one skilled in the art. For example, the carboxy compounds are reacted in an inert solvent with the corresponding arylhydroxy compounds with dicyclohexylcarbodiimide in the presence of a suitable base, for example, pyridine, DMAP, triethylamine, diazabicyclononane (DBN), diazabicycloundecane (DBU). As solvent, methylene chloride, ethylene chloride, chloroform, ethyl acetate, tetrahydrofuran, preferably chloroform, are suitable. The reaction is performed at temperatures between −30° C. and +50° C., preferably at 10° C.

The leukotriene-$B_4$ antagonists of formula I with $R_1$ meaning a COOH group can be converted to a salt with suitable amounts of the corresponding inorganic bases with neutralization. For example, in dissolving the corresponding acids in water, which contains the stoichiometric amount of the base, the solid inorganic salt is obtained after evaporating the water or after adding a water-miscible solvent, e.g., alcohol or acetone.

For the production of an amine salt, the $LTB_4$ acid is dissolved, e.g., in a suitable solvent, for example, ethanol, acetone, diethyl ether, acetonitrile or benzene and at least the stoichiometric amount of the amine is added to this solution. In this way, the salt usually accumulates in solid form or is isolated after evaporation of the solvent in the usual way.

The introduction of amide group $CONHR_3$ takes place according to the methods known to one skilled in the art. The carboxylic acids of formula I ($R_1$=OH) are first converted to the mixed anhydride in the presence of a tertiary amine, such as, for example, triethylamine, with chloroformic acid isobutyl ester. The reaction of the mixed anhydride with the alkali salt of the corresponding amide or with ammonia takes place in an inert solvent or solvent mixture, such as, for example, tetrahydrofuran, dimethoxyethane, dimethylformamide, hexamethylphosphoric acid triamide, at temperatures between −30° C. and +60° C., preferably at 0° C. to 30° C.

The compounds of general formula II used as initial material can be produced, for example, by 2,6-dimethoxybenzaldehyde being reacted with (methoxycarbonylmethylene)-triphenylphosphorane in a Wittig reaction in a way known in the art and converted to the ester of formula IV by subsequent hydrogenation with palladium on carbon in a hydrogen atmosphere.

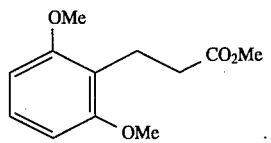   (IV)

By reaction of all methyl groups in IV with 48% HBr and in situ lactonization, the phenol of formula V is obtained

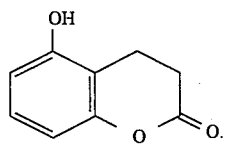   (V)

The phenol of formula V is then reacted with a halide of formula VI

   (VI)

in which Z can be either chlorine, bromine or iodine and X and $R_2$ has the above-indicated meaning under basic conditions, such as, for example, cesium or potassium carbonate, to the compounds of general formula VII

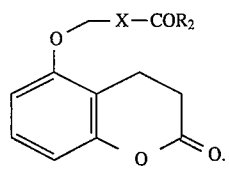   (VII)

The subsequent opening of lactones VII takes place in the desired alcohol under acid catalysis, such as, for example, under sulfuric acid, in this way the desired compounds of general formula II are obtained.

The production of compounds of formula III can be explained based on the following method of synthesis:

1. 2-Hydroxy-3-propyl-4-(3-chloropropyloxy)-acetophenone 6.68 g of potassium carbonate followed by 3.8 ml of 1-bromo- 3-chloropropane are added to a solution of 7.5 g of 2,4-dihydroxy- 3-propyl-acetophenone in 45 ml of DMF under argon and then stirred for 16 hours at 24° C. Then, 50 ml of water is added and extracted three times.with 50 ml of ether each. The combined organic phases are washed once with saturated sodium chloride solution, dried on sodium sulfate and after filtration, concentrated by evaporation in a vacuum. The thus obtained residue is purified by chromatography on silica gel. With hexane/0–30% ethyl acetate, 3.9 g of the title compound is obtained as colorless oil.

IR(CHCl$_3$): 3005, 2965, 2935, 2873, 1627, 1583, 1498, 1470, 1418, 1371, 1268, 1120, 1057 cm$^{-1}$.

2. 2-Hydroxy-3-propyl-4-(3-iodopropyloxy)-acetophenone 17.27 g of sodium iodide is added to a solution of 3.9 g of the above-produced chlorine compound in 40 ml of acetone under argon and stirred for 10 hours at 50° C. Then, the reaction mixture is concentrated by evaporation in a vacuum, and the residue is taken up again in water/ether. After phase separation, the organic phase is washed once with saturated sodium chloride solution, dried on sodium sulfate and after filtration, concentrated by evaporation in a vacuum. The thus obtained 5.05 g of the yellow solid title compound is used for the next reaction step without further purification.

IR(CHCl$_3$): 3005, 2963, 2935, 2875, 1627, 1585, 1499, 1467, 1419, 1371, 1270, 1119, 1048 cm$^{-1}$.

3. 2-Methoxy-3-propyl-4-(3-iodopropyloxy)-acetophenone 2.97 g of potassium carbonate and 3 ml of methyl iodide are added to a solution of 3.9 g of the above-produced iodine compound in 25 ml of DMF under argon at 24° C. and stirred at this temperature for 18 hours. It is diluted with 100 ml of ether, washed once with water, twice with saturated sodium chloride solution, dried on sodium sulfate and after filtration, concentrated by evaporation in a vacuum. The thus obtained residue is purified. by chromatography on silica gel. With hexane/0–20% ethyl acetate, 2.41 g of the title compound is obtained as colorless oil.

IR(CHCl$_3$): 3005, 2968, 2938, 2878, 1673, 1593, 1468, 1416, 1363, 1265, 1118, 1052, 1018 cm$^{-1}$.

4. 2-Methoxy-3-propyl-4-(3-iodopropyloxy)-acetophenone-ethylene ketal 3.1 ml of ethylene glycol and 50 mg of para-toluenesulfonic acid are added to a solution of 5.25 g of the above-produced acetophenone derivative in 50 ml of toluene. After heating 6 hours in a water separator, it is diluted with 80 ml of ether, washed once with saturated sodium bicarbonate solution and once with saturated sodium chloride solution. After the drying on sodium sulfate and filtration, it is concentrated by evaporation in a vacuum. The thus obtained residue is purified by chromatography on silica gel. With hexane/0–40% ether, 3.5 g of the title compound is obtained as colorless oil.

IR(CHCl$_3$): 3005, 2970, 2942, 2880, 1597, 1468, 1413, 1376, 1265, 1185, 1115, 1046 cm$^{-1}$.

The compounds of formula I act in an anti-inflammatory, antiallergic and antiproliferative manner. In addition, they have antimycotic properties. Consequently, the new leukotriene-B$_4$ derivatives of formula I represent valuable pharmaceutical active ingredients. The compounds of formula I are especially suitable for topical administration, since they exhibit a dissociation between desired topical effectiveness and undesirable systemic side effects.

The new leukotriene-B$_4$ derivatives of formula I are suitable in combination with the auxiliary agents and vehicles usual in galenic pharmaceutics for topical treatmentof diseases of the skin, in which leukotrienes play an important role, e.g.: contact dermatitis, eczemas of the most varied types, neurodermatoses, erythrodermia, pruritus vulvae et ani, rosacea, cutaneus lupus erythematosus, psoriasis, lichen ruber planus et verrucosis and similar skin diseases.

In addition, the new leukotriene-B$_4$ antagonists are suitable for treating multiple sclerosis and the symptoms of shock.

The production of the pharmaceutical agent specialties takes place in the usual way by the .active ingredients being converted to the desired form of administration with suitable additives, such as, for example: solutions, ointments, creams or plasters.

In the thus formulated pharmaceutical agents, the active ingredient concentration depends on the form of administration. In lotions and ointments, an active ingredient concentration of 0.0001% to 3% is preferably used.

Further, the new compounds optionally in combination with the usual auxiliary agents and vehicles are also well-suited for the production of inhalants, which can be used to treat allergic diseases of the respiratory system, such as, for example, bronchial asthma or rhinitis.

Further, the new leukotriene-B$_4$ derivatives are also suitable in the form of capsules, tablets or coated tablets, which preferably contain 0.1 to 100 mg of active ingredient or are administered orally or in the form of suspensions, which preferably contain 1–200 mg of active ingredient per dosage unit, and are also administered rectally to treat diseases of the internal organs, in which leukotrienes play an important role, such as, e.g.: allergic diseases of the intestinal tract, such as colitis ulcerosa and colitis granulomatosa.

In these new forms of administration, the new LTB$_4$ derivatives, in addition to the treatment of diseases of internal organs with inflammatory processes, are also suitable for the treatment of diseases in which, leukotriene-dependent, the increased growth and the new formation of cells are important. Examples are leukemia (increased growth of white blood cells) or arteriosclerosis (increased growth of unstriped muscle cells of blood vessels).

The new leukotriene-B$_4$ derivatives can also be used in combination, such as, e.g., with lipoxygenase inhibitors, cyclooxygenase inhibitors, glucocorticoids, prostacyclin agonists, thromboxane antagonists, leukotriene-D$_4$ antagonists, leukotriene-E$_4$ antagonists, leukotriene-F$_4$ antagonists, phosphodiesterase inhibitors, calcium antagonists, PAF antagonists or other known forms of treatment of the respective diseases.

The following embodiments are used for a more detailed explanation of the process according to the invention.

Example 1

5-{2-(2-Ethoxycarbonylethyl)-3-[3-(4-(2-methyl-1,3,dioxolan-2-yl)-3-methoxy-2-propylphenoxy)-propoxy]-phenoxy}-pentanoic acid ethyl ester 1.45 g of cesium carbonate and 1.80 g of 2-methoxy-3-propyl- 4-(3-iodopropyloxy)-acetophenone-ethylene ketal are added to a solution of 1.37 g of 5-[2-(2-ethoxycarbonylethyl)-3-hydroxyphenoxy]-pentanoic acid ethyl ester in 15 ml of DMF under nitrogen at 24° C. and stirred at this temperature for 24 hours. The reaction mixture is then poured on 50 ml of ice water. It is extracted three times with 50 ml of ethyl acetate each, the combined organic phases are washed once with saturated sodium chloride solution, dried on sodium sulfate and after filtration, concentrated by evaporation in a vacuum. The thus obtained residue is purified by chromatography on silica gel. With hexane/ 0–30% ethyl acetate, 1.03 g of the title compound is obtained as colorless oil.

IR(CHCl$_3$): 3035, 2985, 2965, 2940, 2880, 1730, 1596, 1463, 1257, 1183, 1108, 1042 cm$^{-1}$.

The initial material for the above title compound is produced as follows:

1a) (2E)-3-(2,6-Dimethoxyphenyl)-2-propenoic acid methyl ester 35.6 g of (methoxycarbonylmethylene)-triphenylphosphorane is added to a solution of 8.48 g of 2,6-dimethoxybenzaldehyde in 450 ml of tetrahydrofuran under nitrogen and refluxed for 16 hours. It is poured on 200 ml of ice water, extracted three times with ethyl acetate, the combined organic phases are washed once with saturated sodium chloride solution, dried on sodium sulfate and after filtration, concentrated by evaporation in a vacuum. The thus obtained residue is purified by chromatography on silica gel. With hexane/0–40% ethyl acetate, a solid is obtained, which is recrystallized from hexane/toluene. 10.6 g of the title compound is obtained in this-way as crystalline substance (melting point: 76°–78° C).

IR(CHCl$_3$): 3038, 3010, 2970, 2958, 2912, 2850, 1705, 1627, 1598, 1585, 1478, 1438, 1320, 1260, 1183, 1172, 1115 cm$^{-1}$.

1b) 3-(2,6-Dimethoxyphenyl)-propanoic acid methyl ester 1.12 g of palladium/carbon (10%) is added to a solution of 10.6 g of the ester, produced in example 1a), in 300 ml of methanol and stirred in a hydrogen atmosphere for 6 hours. Then, it is filtered on silica gel and rewashed with ethyl acetate. After the concentration by evaporation, 10.4 g of the title compound is obtained as colorless oil.

IR(CHCl$_3$): 3038, 3003, 2957, 2910, 2841, 1730, 1598, 1475, 1450, 1438, 1279, 1255, 1191, 1173, 1112 cm$^{-1}$.

1c) 5-Hydroxy-3,4-dihydrocoumarin 10.4 g of the above-produced ester of example 1b) is heated with 144 ml of 48% aqueous HBr for 16 hours (bath temperature 140° C.). Then, it is poured on 500 ml of ice water and the aqueous phase is saturated with sodium chloride. It is extracted three times with ethyl acetate, the combined organic phases are washed once with saturated sodium chloride solution, dried on sodium sulfate and after filtration, concentrated by evaporation in a vacuum. The thus obtained residue is purified by recrystallization from toluene/ethyl acetate. 4.38 g of the title compound is obtained as orange-colored crystals (melting point 172°–176° C.).

IR(CHCl$_3$): 3603, 3300, 3025, 2990, 2920, 2860, 1768, 1625, 1607, 1469, 1290, 1266, 1252, 1170, 1151, 1042, 1018 cm$^{-1}$.

1d) 5-(4-Ethoxycarbonylbutoxy)-3,4-dihydrocoumarin 3.83 g of cesium carbonate, followed by 1.87 ml of 5-bromopentanoic acid ethyl ester, is added to a solution of 9.65 mg of the phenol, produced in example 1c), in 16 ml of dimethylformamide at 22° C. under nitrogen. After 8 hours of stirring at 22° C. the reaction mixture is poured on 50 ml of ice water. It is extracted three times with 40 ml of ethyl acetate each, the combined organic phases are washed once with saturated sodium chloride solution, dried on sodium sulfate and after filtration, concentrated by evaporation in a vacuum. The thus obtained residue is purified by chromatography on silica gel. With hexane/0–30% ethyl acetate, 1.42 g of the title compound is obtained as colorless oil.

IR(CHCl$_3$): 3035, 2990, 2945, 2920, 2878, 1767, 1729, 1613, 1597, 1463, 1350, 1273, 1255, 1163, 1149, 1087 cm$^{-1}$.

1e) 5-[2-(2-Ethoxycarbonylethyl)-3-hydroxy-phenoxy]-pentanoic acid ethyl ester 0.45 ml of concentrated sulfuric acid is added to a solution of 1.42 g of the ester, produced in example 1d), in 20 ml of ethanol under nitrogen, first heated for 4 hours to 65° C. and then allowed to stir for 16 hours at 22° C. The reaction mixture is poured on 50 ml of ice water, extracted four times with 30 ml of ethyl acetate each, the combined organic phases are washed once with saturated sodium bicarbonate solution and once with a semisaturated sodium chloride solution, dried on sodium sulfate and after filtration, concentrated by evaporation in a vacuum. In this way, 1.37 g of the title compound is obtained as colorless oil, which is used in the next reaction step without further purification.

IR(CHCl$_3$): 3330, 3035, 2985, 2960, 2943, 2878, 1728, 1712, 1610, 1594, 1470, 1378, 1277, 1185, 1161, 1092 cm$^{-1}$.

Example 2

3-{2-(3-Methoxycarbonylphenylmethyloxy)-6-[3-(4-(2-methyl-1,3-dioxolan-2-yl)-3-methoxy-2-propylphenoxy)-propoxy]-phenyl}-propanoic acid methyl ester 3.44 g of cesium carbonate and 4.44 g of 2-methoxy-3-propyl- 4-(3-iodopropyloxy)-acetophenone-ethylene ketal are added to a solution of 3.31 g of 3-[2-(3-methoxycarbonylphenylmethyloxy)- 6-hydroxyphenyl]-propanoic acid methyl ester in 35 ml of DMF under nitrogen at 24° C. and stirred at this temperature for 24 hours. The reaction mixture is then poured on 120 ml of ice water. It is extracted three times with 120 ml of ethyl acetate each, the combined organic phases are washed once with saturated sodium chloride solution, dried on sodium sulfate and after filtration, concentrated by evaporation in a vacuum. The thus obtained residue is purified by chromatography on silica gel. With hexane/0–40% ethyl acetate, 4.6 g of the title compound is obtained as colorless oil.

IR(CHCl$_3$): 3035, 3000, 2957, 2878, 1720, 1593, 1462, 1435, 1290, 1255, 1182, 1106, 1041 cm$^{-1}$.

The initial material for the above title compound is produced as follows:

2a) 5-(3-Methoxycarbonylphenylmethyloxy)-3,4-dihydrocoumarin 9.52 g of cesium carbonate, followed by 6.68 g of 3-bromomethylbenzoic acid methyl ester, are added to a solution of 2.42 g of the phenol, produced in example 1c), in 40 ml of dimethylformamide at 22° C. under nitrogen. After 17 hours of stirring at 22° C., the reaction mixture is poured on 200 ml of ice water. It is extracted four times with 150 ml of ethyl acetate each, the combined organic phases are washed once with semisaturated sodium chloride solution, dried on sodium sulfate and after filtration, concentrated by evaporation in a vacuum. The thus obtained residue is purified by chromatography on silica gel. With hexane/ 0–33% ethyl acetate, 3.05 g of the title compound is obtained as colorless oil.

IR(CHCl$_3$): 3020, 2952, 2910, 1768, 1720, 1613, 1596, 1463, 1291, 1266, 1253, 1169, 1146, 1109, 1077 cm$^{-1}$.

2b) 3-[2-(3-Methoxycarbonylphenylmethyloxy)-6-hydroxyphenyl]-propanoic acid methyl ester 0.62 ml of concentrated sulfuric acid is added to a solution of 3.0 g of the ester, produced in example 2a), in 31 ml of methanol under nitrogen, first heated for 6 hours to 65° C. and then allowed to stir for 16 hours at 22° C. The reaction mixture is poured on 200 ml of ice water, extracted four times with 150 ml of ethyl acetate each, the combined organic phases are washed once with saturated sodium bicarbonate solution, and three times with a semisaturated sodium chloride solution, dried on sodium sulfate and after filtration, concentrated by evaporation in a vacuum. In this way, 3.6 g of the title compound is obtained as colorless oil, which is used in the next reaction step without further purification.

IR(CHCl$_3$): 3605, 3340, 3035, 3010, 2968, 2880, 1718, 1612, 1592, 1470, 1440, 1370, 1293, 1273, 1181, 1082 cm$^{-1}$.

Example 3

3-{2-(4-Methoxycarbonylphenylmethyloxy), 6-[3-(4-(2-methyl-1,3-dioxolan-2-yl)-3-methoxy-2-propylphenoxy)-propoxy]-phenyl}-propanoic acid ethyl ester Analogously to example 2), 583 mg of the title compound is obtained from 440 mg of the phenol produced in example 3a) and 590 mg of 2-methoxy-3-propyl-4-(3-iodopropyloxy)-acetophenone-ethylene ketal as colorless oil.

IR(CHCl$_3$): 3.035, 3005, 2957, 2878, 1719, 1593, 1462, 1434, 1290, 1256, 1180, 1105, 1040 cm$^{-1}$.

The initial material for the above title compound is produced as follows:

3a) 5-(4-Methoxycarbonylphenylmethyloxy)-3,4-dihydrocoumarin

Analogously to example 2a), 421 mg of the title compound is obtained as colorless oil from 605 mg of the phenol produced in example 1c) and 1.67 g of 4-bromomethylbenzoic acid methyl ester.

IR(CHCl$_3$): 3012, 295.2, 2910, 1767, 1720, 1612, 1597, 1465, 1437, 1282, 1252, 1170, 1147, 1110, 1072 cm$^{-1}$.

3b) 3-[2-(4-Methoxycarbonylphenylmethyloxy)-6-hydroxyphenyl]-propanoic acid methyl ester Analogously to example 2b), 442 mg of the title compound is obtained. as colorless oil from 410 mg of the ester, produced in example 3a).

IR(CHCl$_3$): 3608, 3340, 3035, 3010, 2958, 2877, 1719, 1612, 1595, 1470, 1440, 1416, 1370, 1313, 1283, 1180, 1162, 1112, 1088 cm$^{-1}$.

Example 4

5-{2-(2-Ethoxycarbonylethyl)-3-[3-(4-acetyl-3-methoxy-2-propylphenoxy)-propoxy]-phenoxy}-pentanoic acid ethyl ester 30 ml of a mixture of acetic acid/water/tetrahydrofuran in a ratio of 65:35:10 is added to 1.0 g of the title compound, produced in example 1), and stirred for 20 hours at 22° C. Then, it is concentrated by evaporation in a vacuum with addition of toluene. The thus obtained residue is purified by chromatography on silica gel. With hexane/0–40% ethyl acetate, 0.46 g of the title compound is obtained as colorless oil.

IR(CHCl$_3$): 3035, 3005, 2965, 2940, 2880, 1728, 1672, 1590, 1462, 1270, 1183, 1164, 1108 cm$^{-1}$.

Example 5

3-{2-(3-Methoxycarbonylphenylmethyloxy)-6-[3-(4-acetyl-3-methoxy-2-propylphenoxy)-propoxy]-phenyl}-propanoic acid methyl ester Analogously to example 4), 3.22 g of the title compound is obtained as colorless oil from 4.3 g of the title compound, produced in example 2.

IR(CHCl$_3$): 3035, 3005, 2958, 2875, 1721, 1670, 1590, 1462, 1435, 1290, 1267, 1183, 1165, 1110 cm$^{-1}$.

Example 6

5-{2-(2-Carboxyethyl)-3-[3-(4-acetyl-3-methoxy-2-propylphenoxy)propoxy]-phenoxy}-pentanoic acid 5 ml of a 0.5N lithium hydroxide solution and 120 mg of solid lithium hydroxide are added to a solution of 280 mg of the diester, produced in example 4), in a mixture of 2.5 ml of methanol and 4.5 ml of tetrahydrofuran. It is stirred for 20 hours at 22° C., then 10 ml of water is added and adjusted witha 1N sulfuric acid to a pH of 4.5. It is extracted three times with 70 ml of ethyl acetate each, the combined organic phases are washed once with saturated sodium chloride solution, dried on sodium sulfate and after filtration, concentrated by evaporation in a vacuum. The thus obtained residue is purified by chromatography on silica gel. With methylene chloride/0–25% isopropanol, 160 mg of the title compound is-obtained as colorless oil.

IR(CHCl$_3$): 3520, 3095, 3035, 3005, 2960, 2933, 2870, 1710, 1668, 1588, 1460, 1412, 1257, 1182, 1106 cm$^{-1}$.

Example 7

3-{2-(3-Carboxyphenylmethyloxy)-6-[3-(4-acetyl-3-methoxy-2-propylphenoxy)-propoxy]-phenyl}-propanoic acid Analogously to example 6), 264 mg of the title compound is obtained as crystalline compound (melting point: 125° C.) from 339 mg of the title compound produced in example 5), after recrystallization from methylene chloride.

IR(CHCl$_3$): 3410, 3100, 3035, 3005, 2963, 2935, 2873, 1700, 1672, 1590, 1462, 1412, 1289, 1173, 1111 cm$^{-1}$.

Example 8

3-{2-(3-Carboxyphenylmethyloxy)-6-[3-(4-(2-methyl-1,3-dioxolan-2-yl)-3-methoxy-2-propylphenoxy]-propoxy]-phenyl}-propanoic acid 4.6 ml of a 0.5N lithium hydroxide solution and 111 mg of solid lithium hydroxide are added to a solution of 300 mg of the diester, produced in example 2), in a mixture of 2.3 ml of methanol and 4.1 ml of tetrahydrofuran. It is stirred for 20 hours at 22° C. then 10 ml of water is added, and adjusted with a 1N sulfuric acid to a pH of 4.5. It is extracted three times with 70 ml of ethyl acetate each, the combined organic phases are washed once with saturated sodium chloride solution, dried on sodium sulfate and after filtration, concentrated by evaporation in a vacuum. The thus obtained residue is purified by chromatography on silica gel. With hexane/0–40% ethyl acetate, 24 mg of the title compound is obtained as colorless oil.

IR(KBr): 3410, 3090, 2960, 2935, 2890, 2875, 1717, 1700, 1595, 1465, 1410, 1386, 1376, 1262, 1255, 1218, 1188, 1112, 1044 cm$^{-1}$.

Example 9

3-{2-(6-Methoxycarbonylpyridin-2-yl-methyloxy)-6-[3-(4-(2-methyl-1,3-dioxolan-2-yl)-3-methoxy-2-propylphenoxy)-propoxy]-phenyl}propanoic acid methyl ester 0.40 g of cesium carbonate and 0.53 g of 2-methoxy-3-propyl- 4-(3-iodopropyloxy)-acetophenone-ethylene ketal are added to a solution of 386 mg of 3-[2-(6-methoxycarbonylpyridin-2-yl-methyloxy)- 6-hydroxyphenyl]-propanoic acid methyl ester in 4.1 ml of DMF under nitrogen at 24° C. and stirred at this temperature for 4.5 hours. The reaction mixture is then poured on 14 ml of ice water. It is extracted four times with 100 ml of ethyl acetate each, the combined organic phases are washed once with saturated sodium chloride solution, dried on sodium sulfate and after filtration, concentrated by evaporation in a vacuum. The thus obtained residue is purified by chromatography on silica gel. With hexane/0–40% ethyl acetate, 615 mg of the title compound is obtained as colorless oil.

IR(CHCl$_3$): 3036, 3005, 2955, 1728, 1588, 1410, 1257, 1110, 1057 cm$^{-1}$.

The initial material for the above title compound is produced as follows:

9a) 6-(Diphenyl-tert-butylsilyloxymethyl)-2-hydroxymethylpyridine 25 g of 2,6-bis-(hydroxymethyl)-pyridine, dissolved in 125 ml of a mixture of tetrahydrofuran and dimethylformamide in the ratio 1:1, is instilled in a suspension of 7.83 g of sodium hydride (55% in mineral oil) in 350 ml of tetrahydrofuran at 0° C. under nitrogen. After 45 minutes of stirring, 46.8 ml of tert-butyl diphenyl silyl chloride is instilled and stirred for 2 hours at 24° C. The reaction mixture is diluted with 1 l of ether, washed twice with semiconcentrated sodium chloride solution, dried on sodium sulfate and after filtration, concentrated by evaporation in a vacuum. The thus obtained residue is purified by chromatography on silica gel. With hexane/20–60% ethyl acetate, 42.8 g of the title compound is obtained as colorless oil.

IR(Film): 3412, 3071, 29.31, 2857, 1739, 1596, 1428, 1242, 1113, 998, 824, 740 cm$^{-1}$.

9b) 6-(Diphenyl-tert-butylsilyloxymethyl)-2-pyridinecarbaldehyde 100 g of manganese dioxide is added in portions to a solution of 20 g of 6-(diphenyl-tert-butylsilyloxymethyl)-2-hydroxymethylpyridine in 236 ml of toluene at 24° C. under nitrogen and stirred for 24 hours. It is filtered on Celite, rewashed well with toluene and concentrated by evaporation in a vacuum. 19.0 g of the title compound is obtained as colored liquid, which is further used without further purification.

IR(Film): 3070, 2931, 2857, 1715, 1593, 1428, 1210, 1113, 998, 824, 741 cm$^{-1}$.

9c) 6-(Diphenyl-tert-butylsilyloxymethyl)-2-pyridinecarboxylic acid methyl ester A solution of 8.15 g of iodine in 148 ml of methanol is instilled in a solution of 18.29 g of 6-(diphenyl-tert-butylsilyloxymethyl)- 2-pyridinecarbaldehyde and 7.22 g of potassium hydroxidelin 593 ml of methanol at 0° C. under nitrogen. After 1 hour of stirring, iodine solution was again.added and subsequently stirred, and this was also repeated until a complete reaction was discernible in the thin layer. The reaction mixture is concentrated by evaporation in a vacuum up to about 60 ml, mixed with 100 ml of semiconcentrated sodium chloride solution and extracted four times with ether. The combined organic phases are washed once with 60 ml of saturated sodium thiosulfate solution, semiconcentrated sodium. chloride solution, dried on sodium sulfate and after filtration, concentrated by evaporation in a vacuum. 19.4 g of the title compound is obtained, which is further used without further purification.

IR(CHCl$_3$): 3070, 2998, 2957, 285.7, 1727, 1593, 1426, 1314, 1110, 980, 822, 700 cm$^{-1}$.

9d) 6-(Hydroxymethyl)-2-pyridinecarboxylic acid methyl ester

A solution of 3.52 g of 6-(diphenyl-tert-butylsilyloxymethyl)- 2-pyridinecarboxylic acid methyl ester in 87 ml of tetrahydrofuran is mixed at 24° C. under nitrogen with 13.6 g of tetrabutylammonium fluoride-trihydrate and stirred for 2 hours. Then, it is mixed with 32 ml of concentrated sodium chloride solution and extracted four times with ethyl acetate. The combined organic phases are dried on sodium sulfate and after filtration, concentrated by evaporation in a vacuum. The thus obtained residue is purified by chromatography on silica gel. With hexane/50–100% ethyl acetate, 0.92 g of the title compound is obtained as colorless oil.

IR(CHCl$_3$): 3663, 3072, 3008, 2932, 2859, 1727, 1589, 1428, 1114, 821, 703 cm$^{-1}$.

9e) 6-(Chloromethyl)-2-pyridinecarboxylic acid methyl ester 5 ml of thionyl chloride is slowly added to 2.50 g of 6-(hydroxymethyl)-2-pyridinecarboxylic acid methyl ester at 0° C. under nitrogen and stirred for 1 hour. The reaction mixture is concentrated by evaporation in a vacuum. The thus obtained residue is mixed with 15 ml of saturated sodium bicarbonate solution and extracted three times with 25 ml of toluene each. After the drying on sodium sulfate and filtration, it is concentrated by evaporation in a vacuum. 2.37 g of the title compound is obtained, which is further used without further purification.

IR(CHCl$_3$): 3033, 3008, 2954, 1727, 1591, 1439, 1322, 1264, 1133, 1086, 994, 701 cm$^{-1}$.

9f) 5-(6-Methoxycarbonylpyridin-2-yl-methyloxy)-3,4dihydrocoumarin

Analogously to example 2a), 3.00 g of the title compound is obtained from 2.10 g of the phenol produced in example 1c) and 2.37 g of 6-(chloromethyl)-2-pyridinecarboxylic acid methyl ester.

Melting point: 198° C.

IR: 3072, 3001, 2953, 1742, 1725, 1591, 1438, 1321, 1261, 228, 1197, 1169, 1133, 1085, 994, 888, 835, 799, 747 cm$^{-1}$.

9g) 3-[2-(6-Methoxycarbonylpyridin-2-yl-methyloxy)-6-hydroxyphenyl]-propanoic acid methyl ester Analogously to example 2b), 390 mg of the title compound is obtained as brown-colored oil from 350 mg of the ester, produced in example 9f).

IR(CHCl$_3$): 3331, 3033, 3007, 2955, 1727, 1592, 1470, 1441, 1369, 1317, 1237, 1180, 1161, 1139, 1103, 1046, 996, 827 cm$^{-1}$.

Example 10

3-{2-(6-Methoxycarbonylpyridin-2-yl-methyloxy)-6-[3-(4-acetyl-3-methoxy-2-propylphenoxy)-propoxy]-phenyl}-propanoic acid methyl ester Analogously to example 4), 479 mg of the title compound is obtained as colorless oil from 615 mg of the title compound, produced in example 9).

IR(CHCl$_3$): 3037, 3008, 2956, 1728, 1670, 1590, 1464, 1412, 1360, 1269, 1184, 1113, 1062, 811 cm$^{-1}$.

Example 11

3-{2-(6-Carboxypyridin-2-yl-methyloxy)-6-[3-(4-acetyl-3-methoxy-2-propylphenoxy)-propoxy]-phenyl}-propanoic acid Analogously to example 6), 159 mg of the title compound is obtained without purification as pale yellowish oil from 159 mg of the title compound, produced in example 10).

IR(Film): 3450, 3180, 3097, 2963, 2937, 2873, 1735, 1710, 1672, 1590, 1465, 1411, 1360, 1269, 1218, 1184, 1113, 1062, 999, 812 cm$^{-1}$.

Example 12

(E/Z)-3-{2-(3-Methoxycarbonylphenylmethyloxy)-6-[3-(4-(1-methoxypropen-2-yl)-3-methoxy-2-propylphenoxy)-propoxy]-phenyl} propanoic acid methyl ester 0.14 g of potassium-tert-butylate is added to a solution of 0.46 g of methoxymethyltriphenylphosphonium chloride in 2 ml of a mixture of dimethyl sulfoxide and tetrahydrofuran in a ratio 2:1 at 0° C. under nitrogen and stirred for 30 minutes. Then, 200 mg of the title compound, produced in example 5), in 3.7 ml of tetrahydrofuran is added and stirred for 16 hours at 24° C. The reaction mixture is diluted with semiconcentrated sodium chloride solution and extracted three times with ether. After the drying on sodium sulfate and filtration, it is concentrated by evaporation in a vacuum. The thus obtained residue is purified by chromatography on silica gel. With hexane/0–40% ether, 103 mg of the title compound is obtained as colorless oil.

IR(Film): 2954, 2871, 1727, 1655, 1595, 1464, 1410, 1374, 1285, 1219, 1109, 982 cm$^{-1}$.

Example 13

3-{2-(3-Methoxycarbonylphenylmethyloxy)-6-[3-(4-(propen-2-yl)-3-methoxy-2-propylphenoxy)-propoxy]-phenyl}-propanoic acid methyl ester Analogously to example 12), 110 mg of the title compound is obtained as colorless oil from 200 mg of the title compound, produced in example 5), and 300 mg of methyltriphenylphosphonium bromide.

IR(Film): 2954, 2871, 1727, 1595, 1464, 1372, 1288, 1203, 1113, 975, 898 cm$^{-1}$.

Example 14

(E/Z)-3-{2-(3-Carboxyphenylmethyloxy)-6-[3-(4-(1-methoxypropen-2-yl)-3-methoxy-2-propylphenoxy)-propoxy]-phenyl}-propanoic acid Analogously to example 6), 83 mg of the title compound is obtained as colorless oil by column chromatography on silica gel with hexane/0–100% ethyl acetate from 97 mg of the title compound, produced in example 12).

IR(CHCl$_3$): 3508, 3077, 3037, 2950, 2930, 1702, 1594, 1464, 1411, 1256, 1183, 1110 cm$^{-1}$.

Example 15

3-{2-(3-Carboxyphenylmethyloxy)-6-[3-(4-(propen-2-yl)-3-methoxy-2-propylphenoxy)-propoxy]-phenyl}-propanoic acid Analogously to example 6), 23 mg of the title compound is obtained as solid substance by column chromatography on silica gel with hexane/0–10% ethyl acetate from 100 mg of the title compound, produced in example 13). Melting point: 86°–88° C.

IR(KBr): 3440, 3078, 2950, 2938, 1702, 1595, 1472, 1412, 1258, 1123, 895 cm$^{-1}$.

We claim:

1. A leukotriene-B$_4$ antagonist compound of formula I

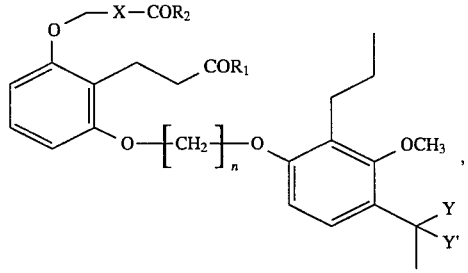

in which n represents a whole number from 2 to 5,

X represents a direct bond, 1 to 6 methylene units, an ortho-, meta- or para-substituted phenyl ring or a meta- or para-substituted pyridine ring, Y represents a hydrogen atom and Y' a hydroxy group, or Y and Y' together represent a double-bound oxygen atom or Y and Y' together represent —O—CH$_2$—CH$_2$—O— forming a ring together with the carbon atom to which they are bound, R$_1$ and R$_2$, independently represent the radical OH, —O—(C$_1$-C$_4$)—alkyl, —O—(C$_3$-C$_6$)—cycloalkyl, —O—(C$_6$-C$_{10}$)—aryl, —O—(C$_7$-C$_{12}$)—aralkyl, O—(CH$_2$) —CO— (C$_6$-C$_{10}$)—aryl or the radical NMR$_3$ with R$_3$ representing hydrogen, (C$_1$-C$_4$)—alkyl, (C$_3$-C$_6$)—cycloalkyl or (C$_7$-C$_{12}$)—aralkyl or a salt thereof with a physiologically compatible base or cyclodextrin clathrate.

2. A pharmaceutical composition comprising a leukotriene-B$_4$ antagonist compound of the formula I of claim 1 and a pharmaceutically acceptable carrier.

3. The compound of claim 1, wherein R$_1$ and R$_2$, independently, are selected from the group consisting of the radicals, hydroxy, methoxy, ethoxy, n-propoxy, isopropoxy, n-butoxy, sec-butoxy, tert-butoxy, cyclopropyloxy, cyclobutyloxy, cyclopentyloxy, cyclohexyloxy, phenoxy, 1-naphthyloxy, 2-naphthyloxy, phenacyl, benzyloxy, phenethoxy, 3-phenylpropoxy, 4-phenylbutoxy, 1-methyl-3-phenylpropoxy, 1-methyl-2-phenylethoxy, amino, methylamino, ethylamino, n-propylamino, isopropylamino, n-butylamino, sec-butylamino, tert-butylamino, cyclopropylamino, cyclobutylamino, cyclopentylamino, cyclohexylamino, benzylamino, phenethylamino, 3-phenylpropylamino, 4-phenylbutylamino, 1-methyl-3phenylpropylamino and 1-methyl-2-phenylethylamino.

4. The compound of claim 1, which is a salt of a physiologically compatible base selected from the group consisting of an alkali hydroxide, an alkaline earth hydroxide, ammonia, ethanolamine, diethanolamine, triethanolamine, n-methylglucamine, morpholine and tris-(hydroxymethyl)-methylamine.

5. The compound of claim 1, which is a clathrate of β-cyclodextrin.

6. The composition of claim 2, in the form of a lotion or ointment.

7. The composition of claim 2, in the form of an inhalant.

8. The composition of claim 2, in the form of a capsule, tablet or coated tablet containing 0.1 to 100 mg of the compound of leukotriene-B$_4$ antagonist compound.

9. The composition of claim 2, in the form of a suspension containing 1 to 200 mg of the compound of leukotriene-B$_4$ antagonist compound.

10. The composition of claim 2, further comprising at least one of a lipoxygenase inhibitor, cyclooxygenase inhibitor, glucocorticoid, prostacyclin agonist, thromboxane antagonist, leukotriene-D$_4$ antagonist, leukotriene-E$_4$ antagonist, leukotriene-F$_4$ antagonist, phosphodiesterase inhibitor, calcium antagonist or PAF antagonist.

11. The compound of claim 1, which is one of the following compounds:

5-{2-(Ethoxycarbonylethyl)-3-[3-(4-(2-methyl-1,3-dioxolan- 2-yl)-3-methoxy-2-propylphenoxy)-propoxy]-phenoxy}pentanoic acid ethyl ester;

3-{2-(3-methoxycarbonylphenylmethyloxy)-6-[3-(4-methyl- 1,3-dioxolan-2-yl)-3-methoxy-2-propylphenoxy)-propoxy]phenyl}-propanoic acid ethyl ester;

3-{2-(4-methoxycarbonylphenylmethyloxy)-6-[3-(2-methyl- 1,3-dioxolan-2-yl)-3-methoxy-2-propylphenoxy)-propoxy]phenyl}-propanoic acid ethyl ester;

5-{2- (2-Ethoxycarbonylethyl)-3-[3-(4-acetyl-3-methoxy- 2-propylphenoxy)-propoxy]-phenoxy}-pentanoic acid ethyl ester;

3-{2-(3-methoxycarbonylphenylmethyloxy)-6-[3-(4-acetyl- 3-methoxy-2-propylphenoxy)-propoxy]-phenyl}-propanoic acid methyl ester;

5-{2-(2-carboxyethyl)-3-[3-(4-acetyl-3-methoxy- 2propylphenoxy)-propoxy]-phenoxy}-pentanoic acid;

3-{2-(3- carboxyphenylmethyloxy)-6-[3-(4-acetyl-3-methoxy- 2-propylphenoxy)-propoxy]-phenyl}-propanoic acid;

3-{2-(3-carboxyphenylmethyloxy)-6-[3-(4-(2-methyl-1,3-dioxolan-2-yl)-3-methoxy-2-propylphenoxy)-propoxy]-phenyl}propanoic acid;

3-{2-(6-methoxycarbonylpyridin-2-yl-methyloxy)-6-[3-(4-(2-methyl-1,3-dioxolan-2-yl)-3-methoxy-2-propylphenoxy)propoxy]-phenyl}-propanoic acid methyl ester;

3-{2-(6-methoxycarbonylpyridin-2-yl-methyloxy)-6-[3-(4-acetyl-3-methoxy-2-propylphenoxy)-propoxy]-phenyl}-propanoic acid methyl ester; and 3-{2-(6-carboxypyridin-2-yl-methyloxy)-6-[3-(4-acetyl-3-methoxy-2-propylphenoxy)-propoxy]-phenyl}-propanoic acid.

* * * * *